United States Patent [19]

Mimura et al.

[11] Patent Number: 5,220,026
[45] Date of Patent: Jun. 15, 1993

[54] PYRAZOLOACRIDONE DERIVATIVES

[75] Inventors: Yukiteru Mimura, Shizuoka; Yasushi Shida, Mishima; Masaji Kasai, Fujisawa; Tadashi Ashizawa, Numazu; Katsushige Gomi, Susono, all of Japan

[73] Assignee: Kyowa Hakko Kogyo Co., Ltd., Tokyo, Japan

[21] Appl. No.: 793,522

[22] Filed: Nov. 18, 1991

[30] Foreign Application Priority Data

Nov. 22, 1990 [JP] Japan .................................. 2-320438

[51] Int. Cl.$^5$ ......................................... C07D 471/16
[52] U.S. Cl. .................................................... 546/66
[58] Field of Search ......................................... 546/66

[56] References Cited

U.S. PATENT DOCUMENTS 4,563,462  1/1986  Ishii ........................ 546/66

FOREIGN PATENT DOCUMENTS 0347749 12/1989  European Pat. Off. .
51-53081  5/1976  Japan .................................... 546/66

OTHER PUBLICATIONS

Ann. Chem. No. 677 (1964) pp. 157–160.

*Primary Examiner*—Marianne M. Cintins
*Assistant Examiner*—Catherine S. Kilby Scalzo
*Attorney, Agent, or Firm*—Fitzpatrick, Cella, Harper & Scinto

[57] ABSTRACT

Disclosed is pyrazoloacridone derivatives represented by formula (I):

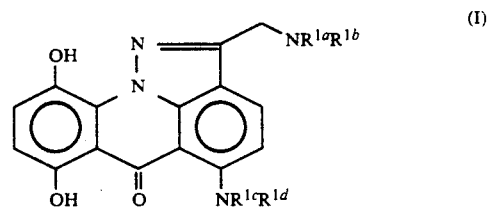

wherein:
each of $R^{1a}$, $R^{1b}$, $R^{1c}$ and $R^{1d}$ independently represents hydrogen, lower alkyl, —$(CH_2)_p$—X wherein p represents an integer of 1 to 6, and X represents hydroxy, lower alkoxy or —$NR^{2a}R^{2b}$ wherein each of $R^{2a}$ and $R^{2b}$ independently represents hydrogen, lower alkyl, or —$(CH_2)_m$—Y wherein m represents an integer of 1 to 6, and Y represents hydroxy, lower alkoxy or —$NR^{3a}R^{3b}$ wherein each of $R^{3a}$ and $R^{3b}$ independently represents hydrogen or lower alkyl
or —$CH[(CH_2)_nOH]_2$ wherein n represents an integer of 1 to 5; or a pharmaceutically acceptable salt thereof.

5 Claims, No Drawings

PYRAZOLOACRIDONE DERIVATIVES

BACKGROUND OF THE INVENTION

The present invention relates to pyrazoloacridone derivatives having anti-tumor activity.

Pyrazoloacridone derivatives having an anti-tumor activity are disclosed in Japanese Published Unexamined Patent Application No. 76878/90 (EP-A-0347749).

The object of the present invention is to provide novel pyrazoloacridone derivatives in which the 7- and 10- positions are hydroxy, and are useful as an anti-tumor agent.

SUMMARY OF THE INVENTION

The present invention relates to pyrazoloacridone derivatives represented by the following. Formula (I) hereinafter, the derivatives of Formula (I) are referred to as Compound (I), and derivative compounds of other formula numbers are referred to similarly:

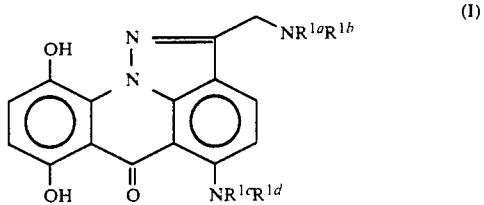

wherein:

each of $R^{1a}$, $R^{1b}$, $R^{1c}$ and $R^{1d}$ independently represents hydrogen, lower alkyl, —$(CH_2)_p$—X
wherein p represents an integer of 1 to 6, and X represents hydroxy, lower alkoxy or —$NR^{2a}R^{2b}$
wherein each of $R^{2a}$ and $R^{2b}$ independently represents hydrogen, lower alkyl, or —$(CH_2)_m$—Y
wherein m represents an integer of 1 to 6, and Y represents hydroxy, lower alkoxy or —$NR^{3a}R^{3b}$
wherein each of $R^{3a}$ and $R^{3b}$ independently represents hydrogen or lower alkyl
or $R^{2a}$ and $R^{2b}$ form a heterocyclic group together with the adjacent nitrogen atom,
or —$CH[(CH_2)_nOH]_2$
wherein n represents an integer of 1 to 5; or a pharmaceutically acceptable salt thereof.

DETAILED DESCRIPTION OF THE INVENTION

In the definition of Formula (I), the lower alkyl and the alkyl moiety in lower alkoxy means a straight or branched alkyl having 1 to 6 carbon atoms such as methyl, ethyl, propyl, isopropyl, butyl, isobutyl, sec-butyl, tertbutyl, pentyl, hexyl, etc. The heterocyclic group to be formed together with the adjacent nitrogen atom includes, for example, pyrrolidinyl, piperidino, piperazinyl and morpholino.

The pharmaceutically acceptable salts of Compound (I) include inorganic acid salts such as hydrochlorides, hydrobromides, sulfates and phosphates, and organic acid salts such as acetates, oxalates, malonates, maleates, fumarates, tartarates, succinates and citrates.

Hereafter, processes for preparing Compound (I) are described. Compound (I) can be obtained from known Compound (II) according to the following reaction steps.

In the processes shown below, in cases where the defined group(s) change under the conditions or are inappropriate for the practice of the processes, the processes can be easily operated by applying thereto means conventionally used in organic synthetic chemistry, for example, protection of functional groups, removal of protective groups, oxidation, reduction and hydrolysis.

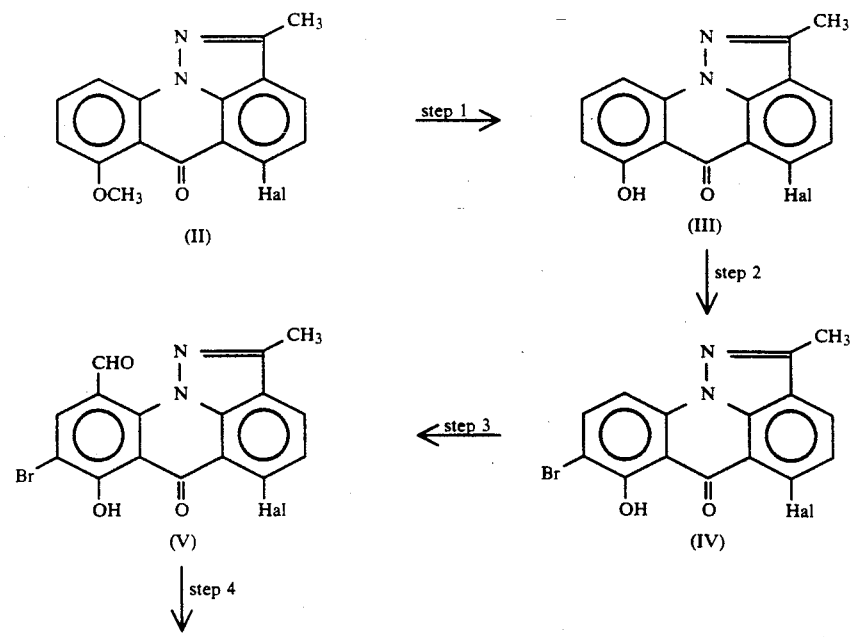

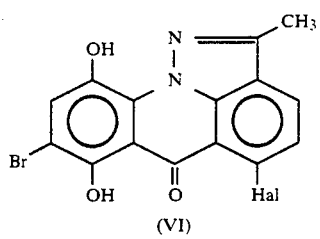
(VI)
-continued
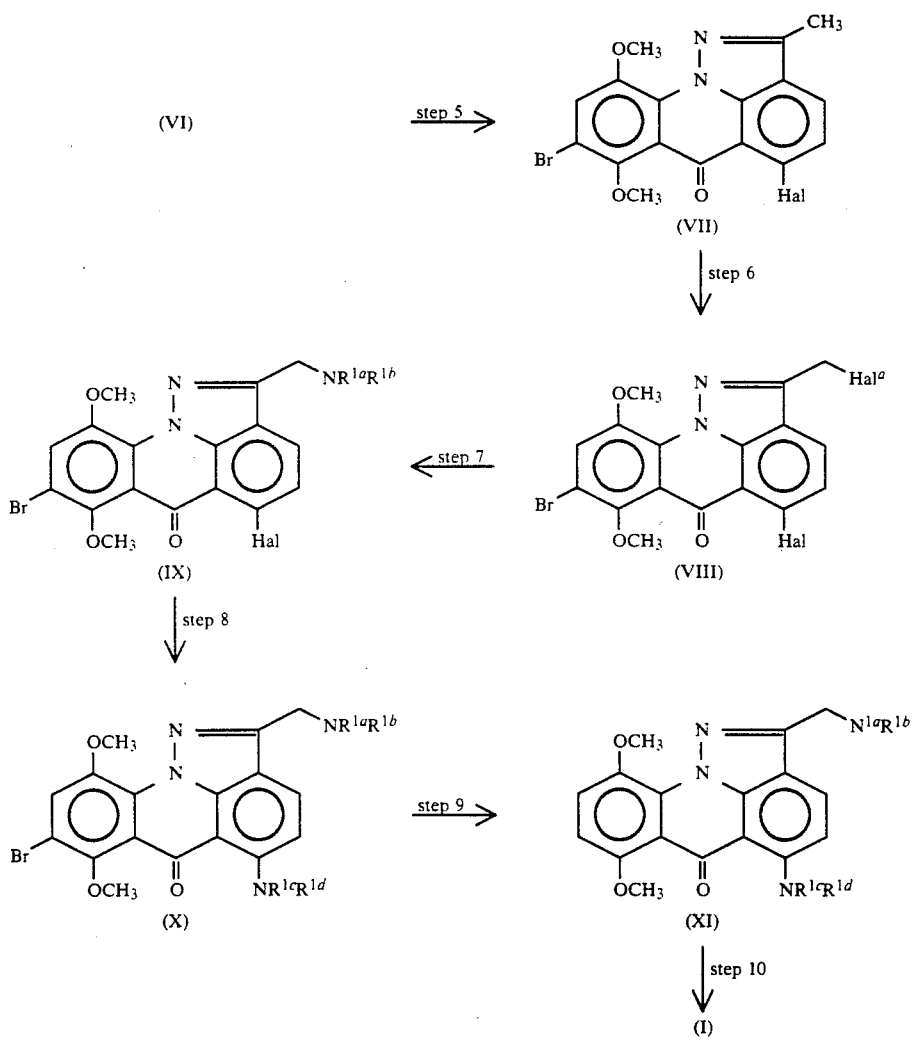
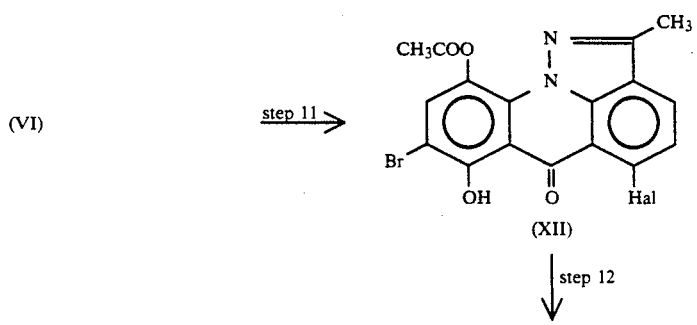

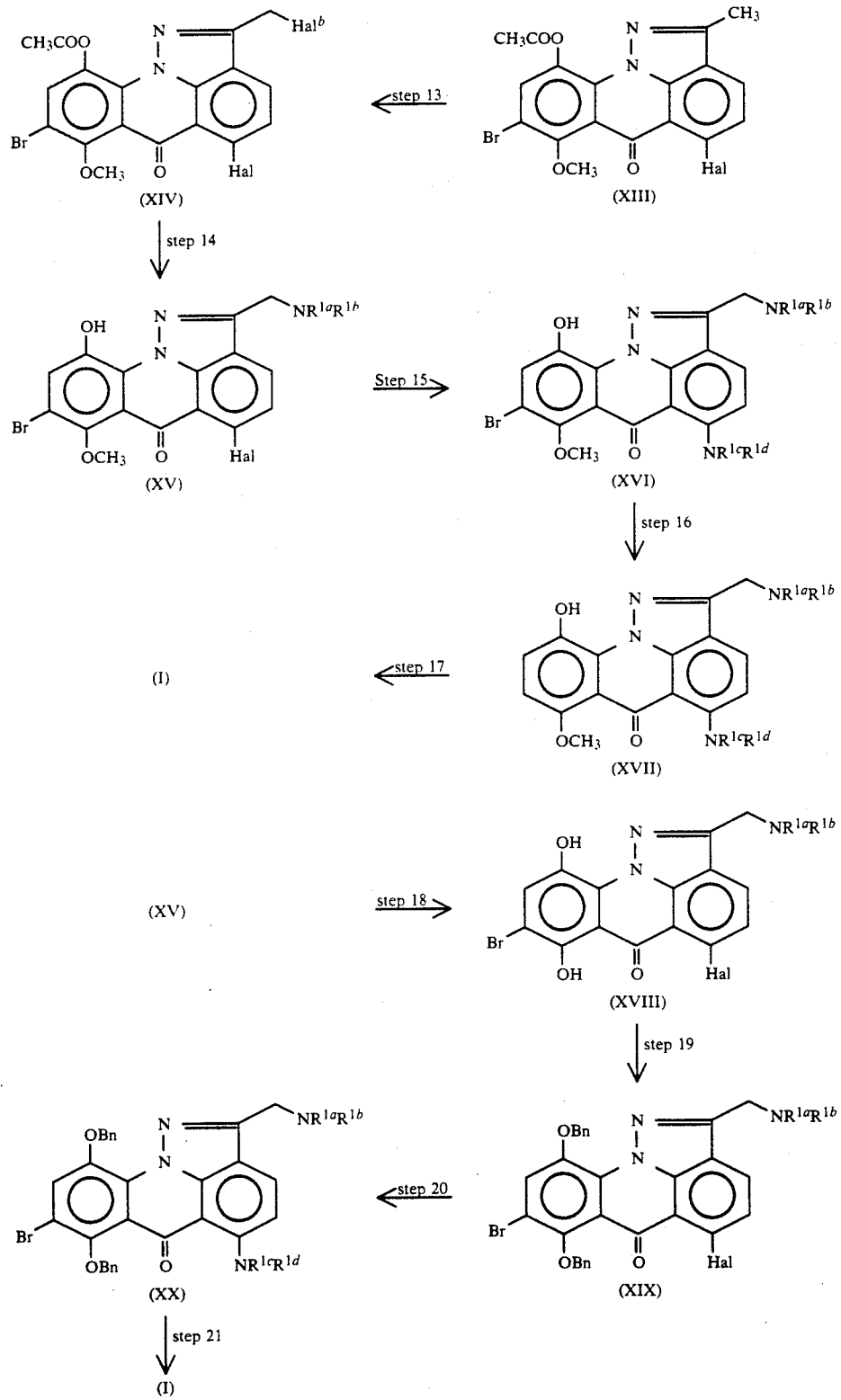

(wherein $R^{1a}$, $R^{1b}$, $R^{1c}$ and $R^{1d}$ are as described above; each of Hal, $Hal^a$ and $Hal^b$ independently represents halogen such as chlorine, bromine or iodine; and Bn represents benzyl.)

Step 1

Compound (III) can be obtained by heating Compound (II) (described in Japanese Published Unexamined Patent Application No. 76878/90) in acetic acid containing 25 to 30% hydrobromic acid.

An amount of hydrobromic acid-containing acetic acid used is in the range of 10 to 300-fold (by weight), preferably 30 to 100-fold, based on Compound (II). The reaction is carried out at 40° to 90° C., preferably 60° to 80° C., and is generally completed in 0.5 to 12 hours.

Step 2

Compound (IV) can be obtained by reacting Compound (III) with bromine in an inert solvent such as chloroform, dichloromethane, 1,2-dichloroethane, etc. under cooling. Bromine is used in an amount of 1 to 3 equivalents, preferably 1 to 1.2 equivalents, based on Compound (III). The reaction is carried out at −80° to 50° C., preferably −50° to 0° C. and completed generally in 0.1 to 5 hours.

Step 3

Compound (V) can be obtained by reacting Compound (IV) with 1 to 50 equivalents of 1,1-dichloromethyl methyl ether in an inert solvent such as dichloromethane or 1,2-dichloroethane in the presence of a Lewis acid catalyst such as titanium tetrachloride, aluminum chloride and tin tetrachloride in an amount of 1 to 100 equivalents based on Compound (IV) and then treating with water. In general, the reaction is carried out at 20° to 60° C. and completed in 0.5 to 24 hours.

Step 4

Compound (VI) can be obtained by reacting Compound (V) with 1 to 3 equivalents of metachloroperbenzoic acid in an inert solvent in the presence of sodium acetate in an amount of 1 to 3 equivalents based on Compound (V). The reaction proceeds generally at 0° to 50° C. and is completed in 0.5 to 24 hours. Examples of the inert solvent include chloroform, dichloromethane, 1 2-dichloroethane, methanol, ethanol, tetrahydrofuran, dioxane and mixtures thereof.

Step 5

Compound (VII) can be obtained by reacting Compound (VI) with a large excess of iodomethane or dimethyl sulfate in an inert solvent in the presence of a base. Preferred examples of the base include potassium carbonate, sodium carbonate, lithium carbonate, sodium hydride, etc. The base may be used in 2 to 4 equivalents based on Compound (VI). The reaction proceeds at 0° to 80° C. and is completed generally in 5 hours to 7 days. Examples of the inert solvent include dimethylformamide, dimethyl sulfoxide, tetrahydrofuran, dioxane and acetone.

Step 6

Compound (VIII) can be obtained by reacting Compound (VII) with 0.9 to 1.1 equivalents of an N-halogenosuccinimide or 0.4 to 0.6 equivalent of 1,3-dibromo-5,5-dimethylhydantoin in an inert solvent in the presence of or absence of a catalyst. As the N-halogenosuccinimide, N-chlorosuccinimide and N-bromosuccinimide are preferably used. Where the catalyst is used, the catalyst such as benzoyl peroxide (BPO) and azobisisobutyronitrile (AIBN) may be used in 0.01 to 0.1 equivalent based on Compound (VII).

As the inert solvent, carbon tetrachloride may be preferably used. The reaction proceeds at room temperature or with heating under reflux and is generally completed in 0.5 to 24 hours.

Step 7

Compound (IX) may be obtained by reacting Compound (VIII) with an amine $HNR^{1a}R^{1b}$ (XXI) or an acid addition salt thereof. Compound (VIII) is allowed to react with the amine (XXI) or its acid addition salt in an inert solvent (or without any solvent), in the presence of a base, if necessary. When no solvent is used, the amine (XXI) can be also used as a solvent in an amount of 1 equivalent to a large excess based on Compound (VIII). Where the acid addition salt of amine (XXI) [for example hydrochloride, hydrobromide, acetate, trifluoroacetate, p-toluenesulfonate (the same shall apply hereinafter)], is used, inorganic bases such as potassium hydroxide, sodium hydroxide, potassium carbonate, sodium carbonate may be used as the base in an amount equimolar to the amine (XXI). Examples of the inert solvent include dimethylformamide, dimethyl sulfoxide, tetrahydrofuran, dioxane, chloroform, dichloromethane, methanol, ethanol, propanol, isopropanol and mixtures thereof. The reaction is carried out preferably at 0° to 40° C. and completed in 1 to 24 hours.

Step 8

Compound (X) can be obtained by reacting Compound (IX) with an amine $HNR^{1c}R^{1d}$ (XXII).

The reaction may be carried out in a manner similar to Step 7. The reaction temperature is preferably 20° to 80° C.

Step 9

Compound (XI) can be obtained by reducing Compound (X). After Compound (X) is converted into its acid addition salt, hydrogenation is carried out in an inert solvent in the presence of a catalyst. Examples of the inert solvent include methanol, ethanol and water. As the catalyst, there may be used palladium on carbon, Raney nickel, etc. The reaction is carried out at room temperature or with heating, preferably at 40° to 60° C. and is completed in 1 to 10 hours.

Step 10

Compound (I) can be obtained by treating Compound (XI) with concentrated hydrobromic acid at 70° to 100° C. in a solvent mixture of acetic acid containing 25 to 30% hydrobromic acid. The reaction is generally completed in 1 to 10 hours.

Step 11

Compound (XII) can be obtained by acetylation of Compound (VI). The reaction is carried out by reacting Compound (VI) with acetic anhydride in an inert solvent in the presence of a base. As the base, there may be used pyridine, triethylamine, etc. Examples of the inert solvent are chloroform, dichloromethane, 1,2-dichloroethane, dimethylformamide, tetrahydrofuran and dioxane. The reaction proceeds at 20° to 60° C. and is completed in 1 to 5 hours.

Step 12

Compound (XIII) can be obtained from Compound (XII) in a manner similar to Step 5.

Step 13

Compound (XIV) can be obtained from Compound (XIII) in a manner similar to Step 6.

Step 14

Compound (XV) can be obtained from Compound (XIV) in a manner similar to Step 7.

Step 15

Compound (XVI) can be obtained from Compound (XV) in a manner similar to Step 8.

Step 16

Compound (XVII) can be obtained from Compound (XVI) in a manner similar to Step 9.

Step 17

Compound (I) can be obtained from Compound (XVII) in a manner similar to Step 10. Compound (I) can also be obtained by treating Compound (XVII) at 60° to 100° C. with concentrated hydrochloric acid for 5 to 10 hours.

Step 18

Compound (XVIII) can be obtained from Compound (XV) in a manner similar to Step 17.

Step 19

Compound (XIX) can be obtained by reacting Compound (XVIII) with 5 to 20 equivalents of benzyl bromide in an inert solvent in the presence of a base. As the base, there may be preferably used potassium carbonate, sodium carbonate, lithium carbonate, sodium hydride, etc. The base may be used in 5 to 20 equivalents based on Compound (XVIII). The reaction proceeds at 0° to 80° C. and is generally completed in 5 hours to 7 days. Examples of the inert solvent include dimethylformamide, dimethyl sulfoxide, tetrahydrofuran, dioxane and acetone.

Step 20

Compound (XX) may be obtained from Compound (XIX) in a manner similar to Step 8.

Step 21

Compound (I) may be obtained from Compound (XX) in a manner similar to Step 9.

The intermediates and the final products obtainable in the processes described above can be isolated and purified by conventional purification methods which are generally employed in organic synthetic chemistry, for example, by filtration, extraction, washing, drying, concentration, recrystallization, various chromatographies.

The intermediates can also be applied directly to the subsequent reaction step without purification.

Where it is desired to obtain the salts of Compound (I), Compound (I) can be purified as it is in case that Compound (I) is obtained in the form of its salts. In case that Compound (I) is obtained in its free form, Compound (I) may be dissolved or suspended in an appropriate organic solvent and an acid is added thereto to form its salts.

Compound (I) and its pharmaceutically acceptable salts may also be present in the form of addition to water or various solvents. These addition products are also included in the present invention.

Typical examples of Compound (I) of the present invention are shown in Table 1.

TABLE 1

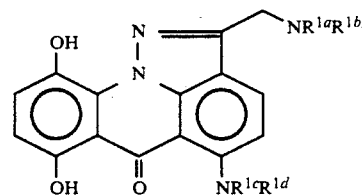

| Compound No | $NR^{1a}R^{1b}$ | $NR^{1c}R^{1d}$ |
|---|---|---|
| 1 | $NH(CH_2)_2NH_2$ | $NH(CH_2)_2NH_2$ |
| 2 | $N(C_2H_5)_2$ | $NH(CH_2)_2NH_2$ |
| 3 | $N(C_2H_5)_2$ | $NH(CH_2)_2N(CH_3)_2$ |
| 4 | $NH(CH_2)_2OH$ | $NH(CH_2)_2NH_2$ |
| 5 | $NH(CH_2)_2OH$ | $NH(CH_2)_3NH_2$ |
| 6 | $NH(CH_2)_2OH$ | $NH(CH_2)_2NH(CH_2)_2OH$ |
| 7 | $NH(CH_2)_2OH$ | $NH(CH_2)_2NHCH_3$ |
| 8 | $NH(CH_2)_2OH$ | $NH(CH_2)_2N(CH_3)_2$ |
| 9 | $N[(CH_2)_2OH]_2$ | $NH(CH_2)_2N(CH_3)_2$ |
| 10 | $NHCH(CH_2OH)_2$ | $NH(CH_2)_2NH_2$ |
| 11 | $NH(CH_2)_2OCH_3$ | $NH(CH_2)_2NH_2$ |
| 12 | $NHCH(CH_2OH)_2$ | $NH(CH_2)_2NH(CH_2)_2OH$ |
| 13 | $NHCH(CH_2OH)_2$ | $NH(CH_2)_3NH_2$ |
| 14 | $NHCH(CH_2OH)_2$ | 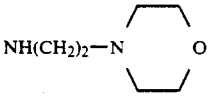 |

Next, the anti-tumor activity of typical examples of Compound (I) is specifically shown referring to experimental examples.

TEST EXAMPLE 1

Effect on sarcoma 180 solid tumor:

Sarcoma 180 tumor cells ($5 \times 10^6$ cells) were implanted intraperitoneally into a ddY mouse and the cells were collected from the ascitic fluid of the mouse 7 days after the implantation. The cells were washed once with sterilized physiological saline solution, and then suspended in sterilized physiological saline solution to prepare a cell suspension containing $5 \times 10^7$ cells/ml. The suspension (0.1 ml) was implanted subcutaneously into the right axilla of a male ddY mouse weighing $20 \pm 2$ g.

A test compound was dissolved in physiological saline solution or Tween 80-containing physiological saline solution, and 0.1 to 0.2 ml of the solution was intravenously administered to 5 mice as one group 24 hours after the implantation of the tumor cells.

The anti-tumor activity of the test compound was determined by measuring the major axis (a) and the minor axis (b) of the tumor 7 days after the implantation of tumor cells to calculate $a \times b^2/2$ corresponding to volume of the tumor. The intended anti-tumor activity is represented by a ratio of T/C, in which C. indicates the tumor volume of mice of the control group to which no test Compound was administered, and T indicates the tumor volume of mice of the test group to which test Compound (I) was administered.

The results are shown in Table 2.

TABLE 2

| Compound No. | Dose (mg/kg) | T/C |
|---|---|---|
| 1 | 25 | 0.10 |
| 2 | 25 | 0.22 |
| 4 | 6.3 | 0.03 |
| 5 | 25 | 0.06 |

TABLE 2-continued

| Compound No. | Dose (mg/kg) | T/C |
|---|---|---|
| 6 | 13 | 0.04 |
| 7 | 3.1 | 0.15 |
| 8 | 6.3 | 0.24 |
| 10 | 25 | 0.05 |
| 11 | 13 | 0.13 |

TEST EXAMPLE 2

Effect on P388 ascites tumor

P388 tumor cells ($10^6$ cells) were implanted intraperitoneally into a DBA/2 mouse and the cells were collected from the ascitic fluid of the animal 7 days after the implantation. The cells were washed once with sterilized physiological saline solution and then suspended in sterilized physiological saline solution to prepare a cell suspension containing $5 \times 10^6$ cells/ml. The suspension (0.2 ml) was inoculated intraperitonally into a male $CDF_1$ mouse aged 6 weeks. A test compound was dissolved in physiological saline solution and intraperitonally to the animal 24 hours after the implantation of the tumor cells. One test group comprised 5 mice. The mean survival time (days) of a test group which received a test compound at a specified concentration was calculated as T from survival days of animals in the group. On the other hand, the mean survival time (days) of the non-administered group (C) was obtained in the same manner, and the increased life span (ILS %) was calculated as $[(T-C)/C] \times 100$ (%).

The results obtained are shown in Table 3.

TABLE 3

| Compound No. | Dose (mg/kg) | ILS (%) |
|---|---|---|
| 1 | 13 | >168 |
| 2 | 13 | 109 |
| 3 | 13 | 87 |
| 5 | 3.1 | >83 |
| 6 | 2.9 | >113 |

The compounds obtained by the present invention exhibit an excellent anti-tumor activity and are useful as anti-tumor agents.

Compounds (I) and their pharmaceutically acceptable salts can be administered directly or in the forms of various pharmaceutical preparations. For instance, when Compounds (I) or their salts are used in the form of injection, they are dissolved in a diluent which is generally used in this technical field such as physiological saline solution or glucose, lactose or mannitol solution for injection. Alternatively, Compound (I) or its salts may be freeze-dried according to the Japanese Pharmacopoeia or may be prepared into injectable powder by adding sodium chloride thereto. The injection may also contain an auxiliary agent such as polyethylene glycol, HCO-60 (surfactant, manufactured by Nikko Chemical Co., Ltd.), ethanol, and/or a carrier such as liposome, cyclodextrin. The injection is generally used for intravenous administration, but can also be administered intramuscularly, intraarterially, intraperitoneally, intrathoracially, etc.

Compounds (I) or their salts may also be formed into tablets, granules, powder or syrup for oral administration with a suitable excipient disintegrator, binder, lubricant in a conventional manner. Furthermore, Compounds (I) or their salts can be mixed with a conventional carrier and formed into suppositories for rectal administration in a conventional manner.

Dosage may appropriately vary according to the kind of Compounds (I) or their salts as well as the age, and condition of a patient, but is generally 1 to 2000 mg/60 kg/day for mammals including human beings. Administration schedule can also be varied according to the condition of a patient or the dosage. For example, the preparation can be intermittently administered once a week or once every 3 weeks.

Hereafter, certain embodiments of the present invention are illustrated in the following examples and reference examples. Intermediates of Compounds (I) are shown in Table 4.

The physicochemical data of each compound were determined by using the following equipments.

| NMR | JEOL, Ltd. | JNM-GX270 (270 MHz) |
|---|---|---|
| MS | JEOL, Ltd. | JMS-D-300 |

TABLE 4

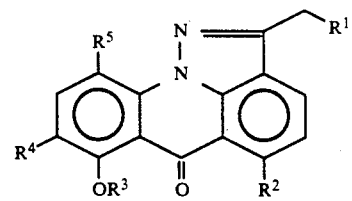

| Compound No | $R^1$ | $R^2$ | $R^3$ | $R^4$ | $R^5$ |
|---|---|---|---|---|---|
| a | H | Br | $CH_3$ | H | H |
| b | H | Br | H | H | H |
| c | H | Br | H | Br | H |
| d | H | Br | H | Br | CHO |
| e | H | Br | H | Br | OH |
| f | H | Br | $CH_3$ | Br | $OCH_3$ |
| g | Br | Br | $CH_3$ | Br | $OCH_3$ |
| h | H | Br | H | Br | $OCOCH_3$ |
| i | H | Br | $CH_3$ | Br | $OCOCH_3$ |
| j | Br | Br | $CH_3$ | Br | $OCOCH_3$ |
| 1a | $NH(CH_2)_2NH_2$ | $NH(CH_2)_2NH_2$ | $CH_3$ | Br | $OCH_3$ |
| 1b | $NH(CH_2)_2NH_2$ | $NH(CH_2)_2NH_2$ | $CH_3$ | H | $OCH_3$ |
| 2a | $N(C_2H_5)_2$ | Br | $CH_3$ | Br | $OCH_3$ |

TABLE 4-continued

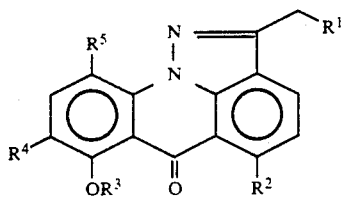

| Compound No | R¹ | R² | R³ | R⁴ | R⁵ |
|---|---|---|---|---|---|
| 2b | $N(C_2H_5)_2$ | $NH(CH_2)_2NH_2$ | $CH_3$ | Br | $OCH_3$ |
| 2c | $N(C_2H_5)_2$ | $NH(CH_2)_2NH_2$ | $CH_3$ | H | $OCH_3$ |
| 3a | $N(C_2H_5)_2$ | $NH(CH_2)_2N(CH_3)_2$ | $CH_3$ | Br | $OCH_3$ |
| 3b | $N(C_2H_5)_2$ | $NH(CH_2)_2N(CH_3)_2$ | $CH_3$ | H | $OCH_3$ |
| 4a | $NH(CH_2)_2OH$ | Br | $CH_3$ | Br | OH |
| 4b | $NH(CH_2)_2OH$ | $NH(CH_2)_2NH_2$ | $CH_3$ | Br | OH |
| 4c | $NH(CH_2)_2OH$ | $NH(CH_2)_2NH_2$ | $CH_3$ | H | OH |
| 5a | $NH(CH_2)_2OH$ | $NH(CH_2)_3NH_2$ | $CH_3$ | Br | OH |
| 5b | $NH(CH_2)_2OH$ | $NH(CH_2)_3NH_2$ | $CH_3$ | H | OH |
| 6a | $NH(CH_2)_2OH$ | $NH(CH_2)_2NH(CH_2)_2OH$ | $CH_3$ | Br | OH |
| 6b | $NH(CH_2)_2OH$ | $NH(CH_2)_2NH(CH_2)_2OH$ | $CH_3$ | H | OH |
| 7a | $NH(CH_2)_2OH$ | $NH(CH_2)_2NHCH_3$ | $CH_3$ | Br | OH |
| 7b | $NH(CH_2)_2OH$ | $NH(CH_2)_2NHCH_3$ | $CH_3$ | H | OH |
| 8a | $NH(CH_2)_2OH$ | $NH(CH_2)_2N(CH_3)_2$ | $CH_3$ | Br | OH |
| 8b | $NH(CH_2)_2OH$ | $NH(CH_2)_2N(CH_3)_2$ | $CH_3$ | H | OH |
| 9a | $N[(CH_2)_2OH]_2$ | Br | $CH_3$ | Br | OH |
| 9b | $N[(CH_2)_2OH]_2$ | $NH(CH_2)_2N(CH_3)_2$ | $CH_3$ | Br | OH |
| 9c | $N[(CH_2)_2OH]_2$ | $NH(CH_2)_2N(CH_3)_2$ | $CH_3$ | H | OH |
| 10a | $NHCH(CH_2OH)_2$ | Br | $CH_3$ | Br | OH |
| 10b | $NHCH(CH_2OH)_2$ | $NH(CH_2)_2NH_2$ | $CH_3$ | Br | OH |
| 10c | $NHCH(CH_2OH)_2$ | $NH(CH_2)_2NH_2$ | $CH_3$ | H | OH |
| 11a | $NH(CH_2)_2OCH_3$ | Br | $CH_3$ | Br | OH |
| 11b | $NH(CH_2)_2OCH_3$ | Br | H | Br | OH |
| 11c | $N(CH_2)_2OCH_3/Bn$ | Br | Bn | Br | OBn* |
| 11d | $N(CH_2)_2OCH_3/Bn$ | $NH(CH_2)_2NH_2$ | Bn | Br | OBn |
| 12a | $NHCH(CH_2OH)_2$ | $NH(CH_2)_2NH(CH_2)_2OH$ | $CH_3$ | Br | OH |
| 12b | $NHCH(CH_2OH)_2$ | $NH(CH_2)_2NH(CH_2)_2OH$ | $CH_3$ | H | OH |
| 13a | $NHCH(CH_2OH)_2$ | $NH(CH_2)_3NH_2$ | $CH_3$ | Br | OH |
| 13b | $NHCH(CH_2OH)_2$ | $NH(CH_2)_3NH_2$ | $CH_3$ | H | OH |
| 14a | $NHCH(CH_2OH)_2$ | $NH(CH_2)_2-N\smile O$ (morpholino) | $CH_3$ | Br | OH |
| 14b | $NHCH(CH_2OH)_2$ | $NH(CH_2)_2-N\smile O$ (morpholino) | $CH_3$ | Br | OH |

*Bn represents benzyl

EXAMPLE 1

5-(2-Aminoethyl)amino-2-(2-aminoethyl)aminomethyl-7,10-dihydroxy-6H-pyrazolo[4,5,1-d,e]acridin-6-one (Compound 1)

Step A

Compound g (500 mg) obtained in Reference Example 7 was added to 10 ml of ethylenediamine, and the mixture was stirred at 55° to 60° C. for 30 minutes. The reaction mixture was concentrated under reduced pressure and the residue was recrystallized twice from methanol and isopropanol to obtain 463 mg (100%) of 5-(2-aminoethyl)amino-2-(2-aminoethyl)aminomethyl-8-bromo-7,10-dimethoxy-6H-pyrazolo[4,5,1-d,e]acridin-6-one (Compound 1a). The compound was recrystallized from hydrobromic acid aqueous solution, methanol and isopropanol to obtain the hydrobromide of Compound 1a.

Step B

The hydrobromide of Compound 1a (557 mg) was dissolved in 8 ml of water and 20 ml of methanol, 100 mg of 10% palladium on carbon was added to the solution. The mixture was stirred for 4.5 hours while heating at 60° C. in a hydrogen flow. After 10% palladium on carbon was filtered off, the filtrate was concentrated under reduced pressure. The residue was recrystallized from water, methanol and ethanol to obtain 283 mg (56.9%) of the hydrobromide of 5-(2-aminoethyl-)amino-2-(2-aminoethyl)aminomethyl-7,10-dimethoxy-6H-pyrazolo[4,5,1-d,e]acridin-6-one (Compound 1b).

Step C

The hydrobromide of Compound 1b (283 mg) was added to 25 ml of 47% hydrobromic acid aqueous solution and 25 ml of 25% hydrobromic acid in acetic acid, the mixture was heated to 100° C. and stirred for 5 hours. The reaction mixture was concentrated to about 10 ml under reduced pressure, and methanol and ethanol were added to the residue. The solids were filtered to give 267 mg (98.7%) of the hydrobromide of Compound 1.

NMR(DMSO-$d_6$) δ(ppm): 3.10–3.16(2H, m), 3.27(2H, t, J=6.7Hz), 3.43(2H, t, J=6.7Hz), 3.88(2H, q, J=6.3Hz), 4.91(2H, s), 6.84(1H, d, J=9.2Hz), 7.28(1H, d, J=9.5Hz), 7.41(1H, d, J=8.9Hz), 7.98(5H, brs), 8.41(1H, d, J=9.2Hz), 9.37(1H, t, J=6.3Hz), 9.65 (1H, s), 13.08(1H, s)

EI-MS(m/z): 382(M+); $C_{19}H_{22}N_6O_3$=382.

EXAMPLE 2

5-(2-Aminoethyl)amino-2-(N,N-diethyl)aminomethyl-7,10-dihydroxy-6H-pyrazolo[4,5,1-d,e]acridin-6-one (Compound 2)

Step A

Compound g (800 mg) obtained in Reference Example 7 was dissolved in 80 ml of chloroform, and then 2.2 g of diethylamine was added thereto, followed by stirring at room temperature for 2 hours. After 50 ml of isopropanol was added to the reaction solution, the mixture was concentrated to about 20 ml under reduced pressure. The crystals precipitated were separated by filtration, whereby 729 mg (92.5%) of 5,8-dibromo-2-(N,N-diethyl)aminomethyl-7,10-dimethoxy-6H-pyrazolo[4,5,1-d,e]acridin-6-one (Compound 2a).

Step B

Compound 2a (367 mg) was added to 3.7 ml of ethylenediamine, and the mixture was stirred at 45° C. for 50 minutes. The reaction mixture was concentrated under reduced pressure. Water and chloroform were added to the residue for extraction. The chloroform layer was concentrated under reduced pressure. The residue was recrystallized from 2 N hydrobromic acid aqueous solution, methanol and isopropanol to obtain 422 mg (90.5%) of the hydrobromide of 5-(2-aminoethyl-)amino-8-bromo-2-(N,N-diethyl)aminomethyl-7,10-dimethoxy-6H-pyrazolo[4,5,1-d,e]acridin-6-one (Compound 2b).

Step C

In the same manner as in Step B in Example 1, the hydrobromide of Compound 2b (406 mg) was subjected to reaction to obtain 330 mg 92.3%) of the hydrobromide of 5-(2-aminoethyl)amino-2-(N,N-diethyl-)aminomethyl-7,10-dimethoxy-6H-pyrazolo[4,5,1-d,e]acridin-6-one (Compound 2c).

Step D

In the same manner as in Step C. in Example 1, the hydrobromide of Compound 2c (309 mg) was subjected to reaction to obtain 270 mg (91.8%) of the hydrobromide of Compound 2.

NMR(DMSO-$d_6$) δ(ppm): 1.33(6H, t, J=7.2Hz), 3.10–3.20 (2H, m), 3.30(4H, q, J=7.0Hz), 3.88(2H, q, J=6.5Hz), 4.95(2H, s), 6.84(1H, d, J=8.9Hz), 7.28 (1H, d, J=9.2Hz), 7.40(1H, d, J=8.9Hz), 7.96(3H, brs), 8.41(1H, d, J=9.2Hz), 9.37(1H, t, J=6.6Hz), 9.65(1H, s), 10.04(1H, brs), 13.05(1H, s). EI-MS(m/z): 395(M+); $C_{21}H_{25}N_5O_3$=395.

EXAMPLE 3

2-(N,N-Diethyl)aminomethyl-5-(2-dimethylaminoethyl)amino-7,10-dihydroxy-6H-pyrazolo[4,5,1-d,e]acridin-6-one (Compound 3)

Step A

Compound 2a (350 mg) obtained in Step A of Example 2 was reacted with 3.5 ml of N,N-dimethylethylenediamine in a manner similar to Step B in Example 2 to obtain a solid. The solid was recrystallized from 1 N hydrochloric acid aqueous solution, methanol and isopropanol to obtain 345 mg (85.4%) of the hydrochloride of 8-bromo-2-(N,N-diethyl)-aminomethyl-5-(2-dimethylaminoethyl)amino-7,10-dimethoxy-6H-pyrazolo[4,5,1-d,e]acridin-6-one (Compound 3a).

In a manner similar to Step B in Example 1, the hydrochloride of Compound 3a (330 mg) was subjected to reaction to obtain 230 mg (80.2%) of the hydrochloride of 2-(N,N-diethyl)aminomethyl-5-(2-dimethylaminoethyl)amino-7,10-dimethoxy-6H-pyrazolo[4,5,1-d,e]acridin-6-one (Compound 3b).

Step C

In a manner similar to Step C. in Example 1, the hydrochloride of Compound 3b (213 mg) was subjected to reaction to obtain 209 mg (88.0%) of the hydrobromide of Compound 3.

NMR(DMSO-$d_6$) δ(ppm): 1.33(6H, t, J=7.3Hz), 2.91(6H, s), 3.30(4H, q, J=6.6Hz), 3.44(2H, t, J=6.3Hz), 4.02(2H, q, J=6.3Hz), 4.96(2H, s), 6.84(1H, d, J=8.9Hz), 7.30(1H, d, J=9.5Hz), 7.41(1H, d, J=8.9Hz), 8.42(1H, d, J=9.2Hz), 9.36(1H, t, J=6.0Hz), 9.65(1H, s), 9.67(1H, brs), 10.01(1H, brs), 13.04(1H, s). EI-MS(m/z): 423(M+); $C_{23}H_{29}N_5O_3$=423.

EXAMPLE 4

5-(2-Aminoethyl)amino-7,10-dihydroxy-2-(2-hydroxyethyl)-aminomethyl-6H-pyrazolo[4,5,1-d,e]acridin-6-one (Compound 4)

Step A

Compound j (3.00 g) obtained 1 in Reference Example 10 was dissolved in 330 ml of chloroform and 90 ml of methanol, and 6.48 ml of ethanolamine was added to the solution. The mixture was stirred at room temperature for 19 hours. Water was added to the reaction mixture for washing. Then the chloroform layer was concentrated under reduced pressure. The residue was subjected to silica gel column chromatography with chloroform - methanol (15:1) as the eluent, and then recrystallized from chloroform and carbon tetrachloride to obtain 1.43 g (50.2%) of 5,8-dibromo-10-hydroxy-2-(2-hydroxyethyl)aminomethyl-7-methoxy-6H-pyrazolo[4,5,1-d,e]acridin-6-one (Compound 4a).

Step B

After Compound 4a (438 mg) was added to 4.4 ml of ethylenediamine, the mixture was stirred at 40° C. for 2.5 hours. The reaction mixture was concentrated under reduced pressure. Water and chloroform were added to the residue for extraction. The chloroform layer was concentrated under reduced pressure. The residue was recrystallized from methanol and isopropanol and further recrystallized from 2 N hydrochloric acid aqueous solution, methanol and isopropanol to obtain 398 mg (82.2%) of the hydrochloride of 5-(2-aminoethyl)amino-8-bromo-10-hydroxy-2-(2-hydroxyethyl)aminomethyl-7-methoxy-6H-pyrazolo[4,5,1-d,e]acridin-6-one (Compound 4b).

Step C

In a manner similar to Step B in Example 1, 375 mg of the hydrochloride of Compound 4b was subjected to reaction to obtain 267 mg (83.6%) of the hydrochloride of 5-(2-aminoethyl)amino-10-hydroxy-2-(2-hydroxyethyl)aminomethyl-7-methoxy-6H-pyrazolo[4,5,1-d,e]acridin-6-one (Compound 4c).

Step D

The hydrochloride of Compound 4c (260 mg) was added to 5 ml of concentrated hydrochloric acid, and the mixture was heated at 90° C. in a sealed tube followed by stirring for 17 hours. The reaction mixture was concentrated under reduced pressure and was recrystallized from water, methanol and ethanol to obtain 223mg (88.9%) of the hydrochloride of Compound 4.

NMR(DMSO-$d_6$) δ(ppm): 3.08–3.13(2H, m), 3.15(2H, t, J=5.4Hz), 3.77(2H, t, J=5.3Hz), 3.89(2H, q, J=6.3Hz), 4.75(2H, s), 5.33(1H, brs), 6.78[1H, d, J=8.8Hz), 7.25(1H, d, J=9.0Hz), 7.36(1H, d, J=9.0Hz), 8.29(2H, brs), 8.36(1H, d, J=9.0Hz), 9.28(1H, t, J=6.2Hz), 9.66(1H, s), 9.79(1H, brs), 13.01(1H, s).

EI-MS(m/z): 383(M+); $C_{19}H_{21}N_5O_4=383$.

EXAMPLE 5

5-(3-Aminopropyl)amino-7,10-dihydroxy-2-(2-hydroxyethyl)-aminomethyl-6H-pyrazolo[4,5,1-d,e]acridin-6-one (Compound 5)

Step A

Compound 4a (477 mg) obtained in Step A of Example 4 and 4.7 ml of 1,3-propanediamine were subjected to reaction in a manner similar to Step B in Example 4 to obtain 415 mg (76.7%) of the hydrochloride of 5-(3-aminopropyl)-amino-8-bromo-10-hydroxy-2-(2-hydroxyethyl)aminomethyl-7-methoxy-6H-pyrazolo[4,5,1-d,e]acridin-6-one (Compound 5a).

Step B

In a manner similar to Step B in Example 1, the hydrochloride of Compound 5a (415 mg) was subjected to reaction to obtain 343 mg (95.7%) of the hydrochloride of 5-(3-aminopropyl)amino-10-hydroxy-2-(2-hydroxyethyl)aminomethyl-7-methoxy-6H-pyrazolo[4,5,1-d,e]acridin-6-one (Compound 5b).

Step C

In a manner similar to Step D in Example 4, the hydrochloride of Compound 5b (342 mg) was subjected to reaction to obtain 313 mg (93.7%) of the hydrochloride of Compound 5.

NMR(DMSO-$d_6$) δ(ppm): 2.01(2H, quint., J=5.5Hz), 2.91-2.97(2H, m), 3.15(2H, t, J=5.3Hz), 3.66-3.72(2H, m), 3.74-3.79(2H, m), 4.75(2H, s), 5.30(1H, brs), 6.80(1H, d, J=8.9Hz), 7.17(1H, d, J=9.2Hz), 7.36 (1H, d, J=9.2Hz), 8.09(3H, brs), 8.35(1H, d, J=9.1Hz), 9.31(1H, t, J=6.3Hz), 9.67(2H, brs), 9.69(1H, s), 13.01(1H, s)

FAB-MS(m/z): 398(M+ +1); $C_{20}H_{23}N_5O_4=397$.

EXAMPLE 6

7,10-Dihydroxy-5-[2-(2-hydroxyethylamino)ethyl]amino-2-(2-hydroxyethyl)aminomethyl-6H-pyrazolo[4,5,1-d,e]acridin-6-one (Compound 6)

Step A

Compound 4a (464 mg) obtained in Step A of Example 4 and 4.6 ml of 2-(2-aminoethylamino)ethanol were subjected to reaction in a manner similar to Step B in Example 4 to obtain 482 mg (100%) of the hydrochloride of 8-bromo-10-hydroxy-5-[2-(2-hydroxyethylamino)ethyl]amino-2-(2-hydroxyethyl)aminomethyl-7-methoxy-6H-pyrazolo[4,5,1-d,e]acridin-6-one (Compound 6a).

Step B

In a manner similar to Step B in Example 1, the hydrochloride of Compound 6a (482 mg) was subjected to reaction to obtain 363 mg (87.0%) of the hydrochloride of 10-hydroxy-5-[2-(2-hydroxyethylamino)ethyl]amino-2-(2-hydroxyethyl)aminomethyl-7-methoxy-6H-pyrazolo[4,5,1-d,e]-acridin-6-one (Compound 6b).

Step C

In a manner similar to Step D in Example 4, the hydrochloride of Compound 6b (338 mg) was subjected to reaction to obtain 296 mg (89.7%) of the hydrochloride of Compound 6

NMR(DMSO-$d_6$) δ(ppm): 3.07(2H, t, J=5.1Hz), 3.15(2H, t, J=5.4Hz), 3.26(2H, t, J=6.2Hz), 3.71(2H, t, J=5.0Hz), 3.77(2H, t, J=5.4Hz), 3.97(2H, q, J=6.4Hz), 4.75(2H, s), 5.30(2H, brs), 6.79(1H, d, J=9.0Hz), 7.28(1H, d, J=9.3Hz), 7.36(1H, d, J=8.8Hz), 8.37(1H, d, J=9.0Hz), 9.23(1H, brs), 9.31 (1H, t, J=6.4Hz), 9.67(1H, s), 9.72(1H, brs), 13.02(1H, s).

EI-MS(m/z): 427(M+); $C_{21}H_{25}N_5O_5=427$.

EXAMPLE 7

7,10-Dihydroxy-2-(2-hydroxyethyl)aminomethyl-5-(2-methylaminoethyl)amino-6H-pyrazolo[4,5,1-d,e]acridin-6-one (Compound 7)

Step A

Compound 4a (477 mg) obtained in Step A of Example 4 and 4.7 ml of N-methylethylenediamine were subjected to reaction in a manner similar to Step B in Example 4 to obtain 425 mg (78.6%) of the hydrochloride of 8-bromo-10-hydroxy-2-(2-hydroxyethyl)aminomethyl-5-(2-methylaminoethyl)amino-7-methoxy-6H-pyrazolo[4,5,1-d,e]acridin-6-one (Compound 7a).

Step B

In a manner similar to Step B in Example 1, the hydrochloride of Compound 7a (425 mg) was subjected to reaction to obtain 342 mg (92.9%) of the hydrochloride of 10-hydroxy-2-(2-hydroxyethyl)aminomethyl-5-(2-methylaminoethyl)amino-7-methoxy-6H-pyrazolo[4,5,1-d,e]acridin-6-one (Compound 7b).

Step C

In a manner similar to Step D in Example 4, the hydrochloride of Compound 7b (323 mg) was subjected to reaction to obtain 297 mg (94.5%) of the hydrochloride of Compound 7.

NMR(DMSO-$d_6$) δ(ppm): 2.62(3H, s), 3.14–3.26(4H, m), 3.75–3.77(2H, m), 3.93–3.96(2H, m), 4.77(2H, s), 5.30(1H, brs), 6.82(1H, d, J=8.8Hz), 7.29(1H, d, J=9.3Hz), 7.39(1H, d, J=8.5Hz), 8.38(1H, d, J=9.3Hz), 9.31–9.36(1H, m), 9.69(1H, s), 13.05(1H, s).

FAB-MS(m/z): 398($M^+$+1); $C_{20}H_{23}N_5O_4$=397.

EXAMPLE 8

7,10-Dihydroxy-5-(2-dimethylaminoethyl)amino-2-(2-hydroxyethyl)aminomethyl-6H-pyrazolo[4,5,1-d,e]acridin-6-one (Compound 8)

Step A

Compound 4a (467 mg) obtained in Step A of Example 4 and 4.6 ml of N,N-dimethylethylenediamine were subjected to reaction in a manner similar to Step B in Example 4 to obtain 412 mg (76.8%) of the hydrochloride of. 8-bromo-5-(2-dimethylaminoethyl)amino-10-hydroxy-2-(2-hydroxyethyl)-aminomethyl-7-methoxy-6H-pyrazolo[4,5,1-d,e]acridin-6-one (Compound 8a).

Step B

In a manner similar to Step B in Example 1, the hydrochloride of Compound 8a (389 mg) was subjected to reaction to obtain 345 mg (100%) of the hydrochloride of 5-(2-dimethylaminoethyl)amino-10-hydroxy-2-(2-hydroxyethyl)aminomethyl-7-methoxy-6H-pyrazolo[4,5,1-d,e]acridin-6-one (Compound 8b)

Step C

In a manner similar to Step D in Example 4, the hydrochloride of Compound 8b (324 mg) was subjected to reaction to obtain 282 mg (89.6%) of the hydrochloride of Compound 8.

NMR(DMSO-$d_6$) δ(ppm): 2.86(6H, s,), 3.16(2H, t, J=5.1Hz), 3.41(2H, t, J=6.5Hz), 3.77(2H, t, J=4.6Hz), 4.03(2H, q, J=6.1Hz), 4.77(2H, s), 5.30 (1H, brs), 6.82(1H, d, J=8.6Hz), 7.30(1H, d, J=9.3Hz), 7.39(1H, d, J=9.0Hz), 8.40(1H, d, J=9.3Hz), 9.31(1H, t, J=6.1Hz), 9.68(1H, s), 9.70(1H, brs), 13.02(1H, s).

FAB-MS(m/z): 412($M^+$+1); $C_{21}H_{25}N_5O_4$=411.

EXAMPLE 9

2-Bis(2-hydroxyethyl)aminomethyl-7,10-dihydroxy-5-(2-dimethylaminoethyl)amino-6H-pyrazolo[4,5,1-d,e]acridin-6-one (Compound 9)

Step A

Compound j (600 mg) obtained in Reference Example 10 was allowed to react with 2.06 ml of diethanolamine in a manner similar to Step A in Example 4 to obtain 251 mg (43.4%) of 2-bis(2-hydroxyethyl)aminomethyl-5,8-dibromo-10-hydroxy-7-methoxy-6H-pyrazolo[4,5,1-d,e]acridin-6-one (Compound 9a) was obtained.

Step B

In a manner similar to Step B in Example 4, Compound 9a (241 mg) was allowed to react with 2.5 ml of N,N-dimethylethylenediamine to obtain 196 mg (71.6%) of the hydrochloride of 2-bis(2-hydroxyethyl)aminomethyl-8-bromodimethylaminoethyl)amino-10-hydroxy-7-methoxy-6H-pyrazolo[4,5,1-d,e]acridin-6-one (Compound 9b).

Step C

In a manner similar to Step B in Example 1, the hydrochloride of Compound 9b (176 mg) was subjected to reaction to obtain 141 mg (90.0%) of the hydrochloride of 2-bis(2-hydroxyethyl)aminomethyl-5-(2-dimethylaminoethyl)-amino-10-hyiroxy-7-methoxy-6H-pyrazolo[4,5,1-d,e]acridin-6-one (Compound 9c).

Step D

The hydrochloride of Compound 9c (121 mg) was subjected to reaction in a manner similar to Step D in Example 4 to obtain 107 mg (92.0%) of the hydrochloride of Compound 9.

NMR(DMSO-$d_6$) δ(ppm): 2.86(6H, s), 3.38–3.43(6H, m), 3.89(4H, t, J=4.9Hz), 4.05(2H, q, J=6.5Hz), 5.02 (2H, s), 5.40(2H, brs), 6.81(1H, d, J=8.8Hz), 7.31(1H, d, J=9.0Hz), 7.37(1H, d, J=9.0Hz), 8.42 (1H, d, J=9.0Hz), 9.30(1H, t, J=6.5Hz), 9.65(1H, s), 10.69(1H, brs), 10.95(1H, brs), 12.98(1H, s).

EI-MS(m/z): 455($M^+$); $C_{23}H_{29}N_5O_5$=455.

Example 10

5-(2-Aminoethyl)amino-7,10-dihydroxy-2-[(1,3-dihydroxyprop-2-yl)amino]methyl-6H-pyrazolo[4,5,1-d,e]acridin-6-one (Compound 10)

Step A

Compound j (750 mg) described in Reference Example 10 and 3.6 g of serinol were subjected to reaction in a manner similar to Step A in Example 4 to obtain 344 mg (46%) of 5,8-dibromo-2-[(1,3-dihydroxyprop-2-yl)amino]methyl-10-hydroxy-7-methoxy-6H-pyrazolo[4,5,1-d,e]acridin-6-one (Compound 10a).

Step B

In a manner similar to Step B in Example 4, Compound 10a (330 mg) was allowed to react with 4 ml of ethylenediamine to obtain 275 mg (82%) of the hydrochloride of 5-(2-aminoethyl)amino-8-bromo-2-[(1,3-dihydroxyprop-2-yl)amino]methyl-10-hydroxy-7-methoxy-6H-pyrazolo[4,5,1-d,e]acridin-6-one (Compound 10b).

Step C

In a manner similar to Step B in Example 1, the hydrochloride of Compound 10b (275 mg) was subjected to reaction to obtain 210 mg (88%) of the hydrochloride of 5-(2-aminoethyl)amino-2-[(1,3-dihydroxyprop-2-yl)amino]-methyl-10-hydroxy-7-methoxy-6H-pyrazolo[4,5,1-d,e]acridin-6-one (Compound 10c).

Step D

The hydrochloride of Compound 10c (200 mg) was subjected to reaction in the same manner as in Step D in Example 4 to obtain 143 mg (74%) of the hydrochloride of Compound 10.

NMR(DMSO-$d_6$) δ(ppm): 3.14–3.27(2H, m), 3.32(1H, m), 3.78(4H, d, J=4.8Hz), 3.89(2H, d, J=6.2Hz), 4.83 (2H, s), 5.39(2H, brs), 6.79(1H, d, J=8.8Hz), 7.25(1H, d, J=9.2Hz), 7.36(1H, d, J=8.8Hz), 8.27 (2H, brs), 8.36(1H, d, J=9.2Hz), 9.30(1H, t, J=6.4Hz), 9.57(1H, brs), 9.67(1H, s), 13.02(1H, s).

EI-MS(m/z): 413($M^+$); $C_{20}H_{23}N_5O_5$=413.

EXAMPLE 11

5-(2-Aminoethyl)amino-7,10-dihydroxy-2-(2-methoxyethyl)-aminomethyl-6H-pyrazolo[4,5,1-d,e]acridin-6-one (Compound 11)

Step A

Compound j (790 mg) described in Reference Example 10 and 2.5 ml of methoxyethylamine were subjected to reaction in a manner similar to Step A in Example 4 to obtain 426 mg (59.1%) of 5,8-dibromo-10-hydroxy-7-methoxy-2-(2-methoxyethyl)aminomethyl-6H-pyrazolo[4,5,1-d,e]acridin-6-one (Compound 11a).

Step B

Compound 11a (426 mg) was added to 6 ml of conc. hydrochloric acid, and the mixture was heated at 65° C. in a sealed tube followed by stirring for 13.5 hours. Methanol was added to the reaction mixture and the crystals precipitated were separated by filtration to obtain 430 mg (97.1%) of the hydrochloride of 5,8-dibromo-7,10-dihydroxy-2-(2-methoxyethyl)aminomethyl-6H-pyrazolo[4,5,1-d,e]acridin-6-one (Compound 11b).

Step C

The hydrochloride of Compound 11b (430 mg), 1.47 g of potassium carbonate and 1.3 ml of benzyl bromide were heated under reflux in 400 ml of acetone for 5 days with stirring. The reaction mixture was filtered. The resulting filtrate was concentrated under reduced pressure. The residue was subjected to silica gel column chromatography with chloroform-acetone (100:1) as the eluent and then recrystallized from chloroform and carbon tetrachloride to obtain 340 mg (49.4%) of 2-[N-benzyl-N-(2-methoxyethyl)]-aminomethyl-7,10-dibenzyloxy-5,8-dibromo-6H-pyrazolo-[4,5,1-d,e]acridin-6-one (Compound 11c).

Step D

Compound 11c (330 mg) was allowed to react with 3.5 ml of ethylenediamine in a manner similar to Step B in Example 4 to obtain 119 mg (35.4%) of the hydrochloride of 5-(2-aminoethyl)amino-2-[N-benzyl-N-(2-methoxyethyl)]-aminomethyl-8-bromo-7,10-dibenzyloxy-6H-pyrazolo[4,5,1-d,e]-acridin-6-one (Compound 11d).

Step E

The hydrochloride of Compound 11d (110 mg) was subjected to reaction in a manner similar to Step B in Example 1 to obtain 66 mg (91.6%) of the hydrochloride of Compound 11.

NMR(DMSO-$d_6$) δ(ppm): 3.12(2H, t, J=5.9Hz), 3.26-3.30 (2H, m), 3.33(3H, s), 3.69(2H, t, J=5.1Hz), 3.88 (2H, q, J=6.4Hz), 4.76(2H, s), 6.82(1H, d, J=8.8Hz), 7.27(1H, d, J=9.3Hz), 7.39(1H, d, J=9.0Hz), 8.15(2H, brs), 8.36(1H, d, J=9.3Hz), 9.33 (1H, t, J=6.4Hz), 9.69(1H, s), 9.70(1H, brs), 13.05(1H, s).

FAB-MS(m/z): 398(M$^+$+1); $C_{20}H_{23}N_5O_4$=397.

EXAMPLE 12

7,10-Dihydroxy-5-[2-(2-hydroxyethylamino)ethyl]amino-2-[(1,3-dihydroxyprop-2-yl)amino]methyl-6H-pyrazolo[4,5,1-d,e]acridin-6-one (Compound 12)

Step A

Compound 10a (61 mg) described in Example 10 was reacted with 1.5 ml of 2-(2-aminoethylamino)ethanol in a manner similar to Step B in Example 4 to obtain 66 mg (91%) of the hydrochloride of 8-bromo-2-[(1,3-dihydroxyprop -2-yl)amino]methyl-10-hydroxy-5-[2-(2-hydroxyethylamino)-ethyl]amino-7-methoxy-6H-pyrazolo[4,5,1-d,e]acridin-6-one (Compound 12a).

Step B

The hydrochloride of Compound 12a (66 mg) was subjected to reaction in a manner similar to Step B in Example 1 to obtain 45 mg (78%) of the hydrochloride of 2-[(1,3-dihydroxyprop-2-yl)amino]methyl-10-hydroxy-5-[2-(2-hydroxyethylamino)ethyl]amino-7-methoxy-6H-pyrazolo[4,5,1 -d,e]acridin-6-one (Compound 12b).

Step C

The hydrochloride of Compound 12b (45 mg) was subjected to reaction in a manner similar to Step D in Example 4 to obtain 30 mg (68%) of the hydrochloride of Compound 12.

NMR(DMSO-$d_6$) δ(ppm): 3.26(2H, m), 3.70(2H, brs), 3.77 (4H, brs),3.97(2H, m), 4.84(2H, s), 5.34(1H, s), 5.44(2H, s), 6.81(1H, d, J=8.9Hz), 7.28(1H, d, J=8.9Hz),7.38(1H, d, J=8.9Hz), 8.38(1H, d, J=8.9Hz), 9.12(2H, brs), 9.34(1H, m), 9.54(2H, brs), 9.71(1H, s), 13.07(1H, s).

FAB-MS(m/z): 458(M$^+$+1); $C_{22}H_{27}N_5O_6$=457.

EXAMPLE 13

5-(3-Aminopropyl)amino-7,10-dihydroxy-2-[(1,3-dihydroxyprop-2-yl)amino]methyl-6H-pyrazolo[4,5,1-d,e]acridin-6-one (Compound 13)

Step A

Compound 10a (61 mg) as described in Example 10 was reacted with 1.5 ml of propanediamine in a manner similar to Step B in Example 4 to obtain 66 mg (96%) of the hydrochloride in 5-(3-aminopropyl)amino-8-bromo-2-[(1,3-dihydroxyprop-2-yl)amino]methyl-10-hydroxy-7-methoxy-6H-pyrazolo[4,5,1-d,e]acridin-6-one (Compound 13a)

Step B

The hydrochloride of Compound 13a (66 mg) was subjected to reaction in a manner similar to Step B in Example 7, to obtain 45 mg (78%) of the hydrochloride of 5-(3-aminopropyl)amino-2-[(1,3-dihydroxyprop-2-yl)-amino]-methyl-10-hydroxy-7-methoxy-6H-pyrazolo[4,5,1-d,e]acridin-6-one (Compound 13b).

Step C

The hydrochloride of Compound 13b (45 mg) was subjected to reaction in a manner similar to Step D in Example 4, to obtain 30 mg (68%) of the hydrochloride of Compound 13.

NMR(DMSO-$d_6$) δ(ppm): 2.02(2H, m), 2.88(2H, m), 3.28 (1H, br), 3.68(2H, m), 3.76(2H, s), 3.78(2H, s), 4.82(2H, s), 5.42(2H, br), 6.79(1H, d, J=8.9Hz), 7.13(1H, d, J=9.2Hz), 7.33(1H, d, J=9.2Hz), 8.18 (3H, s), 8.33(1H, d, J=8.9Hz), 9.25(1H, brs), 9.58(2H, s), 9.68(1H, s), 12.98(1H, s).

FAB-MS(m/z): 428(M+ +1); $C_{21}H_{25}N_6O_5=427$.

EXAMPLE 14

7,10-Dihydroxy-2-[(1,3-dihydroxyprop-2-yl)amino]-methyl-5-(2-morpholinoethyl)amino-6H-pyrazolo[4,5,1-d,e]acridin-6-one (Compound 14)

Step A

Compound 10a (61 mg) described in Example 10 was reacted with 1.5 ml of 2-(morpholinoethyl)amine in a manner similar to Step B in Example 4 to obtain 62 mg (94%) of the hydrochloride of 8-bromo-2-[(1,3-dihydroxyprop-2-yl)-amino]methyl-10-hydroxy-7-methoxy-5-(2-morpholinoethyl)-amino-6H-pyrazolo[4,5,1-d,e]acridin-6-one (Compound 14a).

Step B

The chloride of 14a (62 mg) was subjected to reaction in a manner similar to Step B in Example 1 to obtain 44 mg (81%) of the hydrochloride of 2-[(1,3-dihydroxyprop-2-yl)amino]methyl-10-hydroxy-7-methoxy-5-(2-morpholinoethyl)-amino-6H-pyrazolo[4,5,1-d,e]acridin-6-one (Compound 14b).

Step C

The hydrochloride (44 mg) of Compound 14b was subjected to reaction in a manner similar to Step D in Example 4 to obtain the hydrochloride (30 mg) of Compound 14. The hydrochloride obtained was dissolved in 25 ml of water and 2.5 ml of methanol, and then 1 N sodium hydroxide aqueous solution was added thereto to adjust the pH of the mixture to 8.0. The crystals precipitated in the solution were separated by filtration, washed with water and then dried in vacuo to obtain 12 mg (32%) of Compound 14.

NMR(DMSO-$d_6$) δ(ppm): 2.69(3H, m), 3.31(2H, brs), 3.43 (6H, brs), 3.65(7H, brs), 4.25(2H, s), 4.48(2H, brs), 6.73(1H, d, J=8.9Hz), 6.95(1H, d, J=9.2Hz), 7.29(1H, d, J=8.9Hz), 8.24(1H, d, J=9.2Hz), 9.43 (1H, brs), 9.97(1H, br), 13.10(1H, s).

FAB-MS(m/z): 484(M+ +1); $C_{24}H_{29}N_5O_6=483$.

REFERENCE EXAMPLE 1

5-Bromo-7-methoxy-2-methyl-6H-pyrazolo[4,5,1-d,e]acridin-6-one (Compound a)

Step A

3-Methyl-6-nitroindazole (5.31 g), 6.93 g of 2-bromo-6-methoxybenzoic acid, 4.71 g of potassium carbonate and 0.218 g of copper (II) oxide were stirred in 60 ml of nitrobenzene at 180° C. for 50 minutes. After cooling, 300 ml of water was added to the reaction mixture, and the insoluble substance was removed by filtration. The resulting solution was washed with chloroform. The aqueous layer was decolored with active charcoal and filtered, and 40 ml of 1 N hydrochloric acid aqueous solution was added to the filtrate. The crystals precipitated were separated by filtration and dried under reduced pressure to obtain 7.45 g (75.9%) of 1-(2-carboxy-3-methoxyphenyl)-3-methyl-6-nitroindazole.

Step B

The compound (7.42 g) described above was suspended in 74 ml of ethanol, and 0.34 g of 10% palladium on carbon was added thereto, followed by stirring at 50° C. Then, 3.35 ml of hydrazine monohydrate was gradually added dropwise to the suspension, and then the mixture was heated under reflux with stirring for further 2 hours. After cooling, the reaction mixture was filtered through a pad of Celite and the filtrate was concentrated to obtain 7.20 g (100%) of 6-amino-1-(2-carboxy-3-methoxyphenyl)-3-methylindazole.

Step C

To the compound (7.20 g) described above was added 144 g of polyphosphoric acid, and the mixture was stirred at 140° to 160° C. for 2 hours. After cooling, the reaction mixture was poured into water. The crystals precipitated were separated by filtration, washed with water and then dried under reduced pressure. The crystals were subjected to silica gel column chromatography with chloroform:acetone (9:1) as the eluent. The fraction showing Rf value of 0.3 in silica gel thin layer chromatography (developing solvent; chloroform:acetone=9:1) was collected to obtain 1.83 g (28.9%) of 5-amino-7-methoxy-2-methyl-6H-pyrazolo[4,5,1-d,e]acridin-6-one.

Step D:

The compound (1.67 g) described above was added to a mixture of 4.6 ml of sulfuric acid, 0.46 g of sodium nitrite and 11 ml of acetic acid, the mixture was stirred at room temperature for 30 minutes. Then, the mixture was added to a solution of 1.90 g of copper (I) bromide in 11 ml of concentrated hydrobromic acid and the mixture was stirred at room temperature for 30 minutes. The reaction mixture was added to 400 ml of ice water and the solid formed was separated by filtration. The solid was heated to reflux in 400 ml of chloroform. After insoluble substances were removed by filtration, the chloroform layer was washed with water, dried over anhydrous sodium sulfate and then concentrated under reduced pressure. The residue was recrystallized from chloroform and isopropyl ether to obtain 1.72 g (83.9%) of Compound a.

NMR(DMSO-$d_6$) δ(ppm): 2.70(3H, s), 3.94(3H, s), 7.04 (1H, dd, J=1.1, 8.2Hz), 7.69(1H, dd, J=1.1, 8.1Hz), 7.72(1H, d, J=8.2Hz), 7.78(1H, t, J=8.2Hz), 8.10(1H, d, J=8.2Hz).

EI-MS(m/z): 342, 344(M+); $C_{16}H_{11}{}^{79}BrN_2O_2=342$.

REFERENCE EXAMPLE 2

5-Bromo-7-hydroxy-2-methyl-6H-pyrazolo[4,5,1-d,e]acridin-6-one (Compound b)

Compound a (1.60 g) obtained in Reference Example 1 was allowed to react with 50 ml of 25% hydrobromic acid in acetic acid at 70° C. for 2 hours, and then of water was added to the reaction mixture. The crystals precipitated were filtered, and recrystallized from chloroform, carbon tetrachloride and isopropyl alcohol to obtain 1.39 g (90.8%) of Compound b as crystals.

NMR(DMSO-$d_6$) δ(ppm): 2.71(3H, s), 6.83(1H, d, J=8.2Hz), 7.50(1H, d, J=7.9Hz), 7.76(1H, t, J=8.2Hz), 7.82 (1H, d, J=8.2Hz), 8.23(1H, d, J=7.9Hz), 14.12(1H, s).

EI-MS(m/z): 328, 330(M+); $C_{15}H_9{}^{79}BrN_2O_2=328$.

REFERENCE EXAMPLE 3

5,8-Dibromo-7-hydroxy-2-methyl-6H-pyrazolo[4,5,1-d,e]-acridin-6-one (Compound c)

Compound b (7.36 g) obtained in Reference Example 2 was dissolved in 1.7 l of chloroform, and the solution was cooled to −40° C. and 400 ml of chloroform containing 1.27 ml of bromine was added thereto, followed by stirring for 30 minutes. The reaction mixture was concentrated to about 200 ml under reduced pressure. The crystals precipitated were separated by filtration to give 8.64 g (94.7%) of Compound c.

NMR(DMSO-$d_6$) $\delta$(ppm): 2.74(3H, s), 7.54(1H, d, J=8.9Hz), 7.91(1H, d, J=7.9Hz), 8.07(1H, d, J=8.9Hz), 8.32 (1H, d, J=7.9Hz), 14.19(1H, s).

EI-MS(m/z): 406, 408, 410(M+); $C_{15}H_8{}^{79}Br_2N_2O_2 = 406$.

REFERENCE EXAMPLE 4

5,8-Dibromo-10-formyl-7-hydroxy-2-methyl-6H-pyrazolo[4,5,1-d,e]acridin-6-one (Compound d)

Compound c (8.64 g) obtained in Reference Example 3 was dissolved in 2.6 l of 1,2-dichloroethane with heating, and 200 ml of titanium tetrachloride and 50 g of dichloromethyl methyl ether were added thereto. The reaction temperature was kept at 55° C. After stirring for 4 hours, the reaction mixture was poured into 2 l of ice water while stirring. The 1,2-dichloroethane layer was washed with water, dried over anhydrous sodium sulfate and then concentrated to about 400 ml under reduced pressure. The crystals precipitated were separated by filtration to obtain 7.70 g (83.4%) of Compound d.

NMR(CDCl$_3$) $\delta$(ppm): 2.78(3H, s), 7.88(1H, d, J=8.1Hz), 7.94(1H, d, J=8.1Hz), 8.59(1H, s), 11.45(1H, s), 15.41(1H, s)

EI-MS(m/z): 434, 436, 438(M+); $C_{16}H_8{}^{79}Br_2N_2O_3 = 434$.

REFERENCE EXAMPLE 5

5,8-Dibromo-7,10-dihydroxy-2-methyl-6H-pyrazolo[4,5,1-d,e]-acridin-6-one (Compound e)

Compound d (7.65 g) obtained in Reference Example 4 was dissolved in 2.1 l of chloroform, and then 6.44 g of metachloroperbenzoic acid (purity of 85%), 2.45 g of sodium acetate and 680 ml of methanol were added thereto, followed by stirring at room temperature overnight. The reaction mixture was washed with aqueous solution of 6.0 g of sodium thiosulfate and dried over anhydrous sodium sulfate. The mixture was concentrated to about 200 ml under reduced pressure. The crystals precipitated were separated by filtration to obtain 5.91 g (79.4%) of Compound e.

NMR(CDCl$_3$) $\delta$(ppm): 2.77(3H, s), 7.55(1H, s), 7.78 (1H, d, J=8.4Hz), 7.90(1H, d, J=8.1Hz), 9.61(1H, s), 13.30(1H, s).

EI-MS(m/z): 422, 424, 426(M+); $C_{15}H_8{}^{79}Br_2N_2O_2 = 422$.

REFERENCE EXAMPLE 6

5,8-Dibromo-7,10-dimethoxy-2-methyl-6H-pyrazolo[4,5,1-d,e]-acridin-6-one (Compound f)

Compound e (2.88 g) obtained in Reference Example 5, 2.88 g of potassium carbonate and 90 ml of iodomethane were heated under reflux in 1.5 l of acetone with stirring for 7 days. The reaction mixture was concentrated under reduced pressure. Chloroform and water were added to the residue for extraction. The chloroform layer was dried over anhydrous sodium sulfate and concentrated under reduced pressure. The residue was recrystallized from chloroform, carbon tetrachloride and isopropanol to obtain 2.86 g (93.2%) of Compound f.

NMR(CDCl$_3$) $\delta$(ppm): 2.77(3H, s), 4.03(3H, s), 4.07 (3H, s), 7.58(1H, s), 7.77(1H, d, J=8.1Hz), 7.79 (1H, d, J=8.1Hz).

EI-MS(m/z); 450, 452, 454(M+); $C_{17}H_{12}{}^{79}Br_2N_2O_3 = 450$.

REFERENCE EXAMPLE 7

2-Bromomethyl-5,8-dibromo-7,10-dimethoxy-2-6H-pyrazolo[4,5,1-d,e]acridin-6-one (Compound g)

Compound f (2.66 g) obtained in Reference Example 6, 1.07 g of N-bromosuccinimide and 71 mg of benzoyl peroxide were heated in 600 ml of carbon tetrachloride for 24 hours with stirring. The reaction mixture was concentrated under reduced pressure. After the residue was subjected to silica gel column chromatography with chloroform - acetone (100:1) as the eluent, the residue was recrystallized from chloroform, carbon tetrachloride and isopropanol to obtain 1.60 g (51.3%) of Compound g.

NMR(CDCl$_3$) $\delta$(ppm): 4.03(3H, s), 4.07(3H, s), 4.93(2H, s), 7.60(1H, s), 7.82(1H, d, J=8.1Hz), 8.01(1H, d, J=8.1Hz).

EI-MS(m/z): 528, 530, 532, 534(M+); $C_{17}H_{11}{}^{79}Br_3N_2O_3 = 528$.

REFERENCE EXAMPLE 8

10-Acetoxy-5,8-dibromo-7-hydroxy-2-methyl-6H-pyrazolo-[4,5,1-d,e]acridin-6-one (Compound h)

Compound e (1.40 g) obtained in Reference Example 5, 30 ml of acetic anhydride and 20 ml of pyridine in 300 ml of chloroform were heated under reflux for 4 hours with stirring. The reaction mixture was concentrated to about 100 ml under reduced pressure and 100 ml of carbon tetrachloride was added thereto. The crystals precipitated were separated by filtration to obtain 1.01 g (65.7%) of Compound h.

NMR(CDCl$_3$) $\delta$(ppm): 2.47(3H, s), 2.71(3H, s), 7.70 (1H, s), 7.85(2H, ABq), 14.40(1H, s).

EI-MS(m/z): 464, 466, 468(M+); $C_{17}H_{10}{}^{79}Br_2N_2O_4 = 464$.

REFERENCE EXAMPLE 9

10-Acetoxy-5,8-dibromo-7-methoxy-2-methyl-6H-pyrazolo-[4,5,1-d,e]acridin-6-one (Compound i)

Compound h (1.00 g) obtained in Reference Example 8, 0.30 g of potassium carbonate and 30 ml of iodomethane were subjected to reaction in a manner similar to Reference Example 6 to obtain 0.98 g (95.0%) of Compound i.

NMR(CDCl$_3$) $\delta$(ppm): 2.49(3H, s), 2.69 (3H,s) 4.07(3H s), 7.72(1H, s), 7.76(2H, brs)

EI-MS(m/z): 478, 480, 482(M+); $C_{18}H_{12}{}^{79}Br_2N_2O_4 = 478$.

REFERENCE EXAMPLE 10

10-Acetoxy-2-bromomethyl-5,8-dibromo-7-methoxy-6H-pyrazolo-[4,5,1-d,e]acridin-6-one (Compound j)

Compound i (6.62 g) obtained in Reference Example 9, 2.50 g of N-bromosuccinimide and 167 mg of benzoyl chloride were subjected to reaction in a manner similar to Reference Example 7 to obtain 4.01 g (52.0%) of Compound j.

NMR(CDCl$_3$) $\delta$(ppm): 2.49(3H, s), 4.07(3H, s), 4.08 (2H, s), 7.71(1H, s), 7.79(1H, d, J=8.4Hz), 7.98 (1H, d, J=8.1 Hz)

FAB-MS(m/z); 557, 559, 561, 563(M++1); $C_{18}H_{11}{}^{79}Br_3N_2O_4=556$.

What is claimed is:

1. A pyrazoloacridone derivative represented by formula (I):

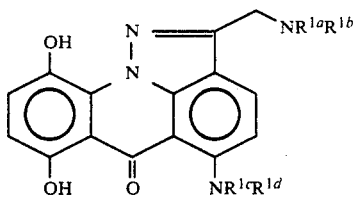

wherein: each of $R^{1a}$, $R^{1b}$, $R^{1c}$ and $R^{1d}$ independently represents hydrogen, lower alkyl, —$(CH_2)_p$—X, wherein p an integer of 1 to 6, and X represents hydroxy, lower alkoxy or —$NR^{2a}R^{2b}$ wherein each of $R^{2a}$ and $R^{2b}$ independently represents hydrogen, alkyl, or —$(CH_2)_m$—Y wherein m an integer of 1 to 6, and Y represents hydroxy, lower alkoxy or —$NR^{3a}R^{3b}$, wherein $R^{3a}$ and $R^{3b}$ independently represents hydrogen or lower alkyl or —$CH[(CH_2)_nOH]_2$, and wherein n represents an integer of 1 to 5; or a pharmaceutically acceptable salt thereof.

2. The compound according to claim 1, wherein $NR^{1a}R^{1b}$ is $NH(CH_2)_2OH$.

3. The compound according to claim 1, wherein $NR^{1c}R^{1d}$ is $NH(CH_2)_3NH_2$ or $NH(CH_2)_2NH(CH_2)_2OH$.

4. The compound according to any one of claims 1, 2 and 3, wherein $NR^{1a}R^{1b}$ is $NH(CH_2)_2OH$ or $NR^{1c}R^{1d}$ is $NH(CH_2)_3NH_2$.

5. The compound according to any one of claims 1, 2 and 3, wherein $NR^{1a}R^{1b}$ is $NH(CH_2)_2OH$ or $NR^{1c}R^{1d}$ is $NH(CH_2)_2NH(CH_2)_2OH$.

* * * * *

UNITED STATES PATENT AND TRADEMARK OFFICE
CERTIFICATE OF CORRECTION

PATENT NO. : 5,220,026
DATED : June 15, 1993
INVENTOR(S) : YUKITERU MIMURA, ET AL.

It is certified that error appears in the above-identified patent and that said Letters Patent is hereby corrected as shown below:

COLUMN 1

Line 17, "following." should read --following--.
Line 18, "hereinafter," should read --[hereinafter,--.
Line 20, "similarly:" should read --similarly]:--.
Line 33, "-(CH$_2$)$_p$-X" should read -- -(CH$_2$)$_p$-X,--.
Line 37, "-(CH$_2$)$_m$-Y" should read -- -(CH$_2$)$_m$-Y,--.

COLUMN 2

Line 2, "-NR$^{3a}$R$^{3b}$" should read -- -NR$^{3a}$R$^{3b}$,--.
Line 4, "alkyl" should read --alkyl,--.

COLUMN 10

TABLE 1, Line 19, "8   NH(CH$_2$)$_2$OH   NH(CH$_2$)$_2$N)CH$_3$)$_2$"

should read --8   NH(CH$_2$)$_2$OH   NH(CH$_2$)$_2$N(CH$_3$)$_2$--.

COLUMN 11

Line 20, "intraperitonally" should read
--intraperitoneally--.
Line 23, "and intraperitonally" should read --and
administered intraperitoneally--.

COLUMN 15

Line 30, "(Compound 2)" should read --(Compound 2).--
and close up left margin.

UNITED STATES PATENT AND TRADEMARK OFFICE
CERTIFICATE OF CORRECTION

PATENT NO. : 5,220,026
DATED : June 15, 1993
INVENTOR(S) : YUKITERU MIMURA, ET AL.

It is certified that error appears in the above-identified patent and that said Letters Patent is hereby corrected as shown below:

COLUMN 16

Line 14, "(Compound 3)" should read --(Compound 3).--
and close up left margin.
Line 49, "(Compound 4)" should read --(Compound 4).--
and close up left margin.
Line 52, "1" should be deleted.

COLUMN 17

Line 40, "(Compound 5) should read --(Compound 5).--
and close up left margin.

COLUMN 18

Line 9, "(Compound 6)" should read --(Compound 6).--.
Line 33, "Compound 6" should read --Compound 6.--.
Line 46, "(Compound 7) should read --(Compound 7).--
and close up left margin.

COLUMN 19

Line 13, "(Compound 8) should read --(Compound 8).--
and close up left margin.
Line 31, "(Compound 8b) should read --(Compound 8b).--.
Line 49, "(Compound 9) should read --(Compound 9).--.
Line 66, "8-bromodimethylaminoethyl)amino" should read
--8-bromo-dimethylaminoethyl)amino--.

COLUMN 20

Line 7, "10-hyiroxy" should read --10-hydroxy--.

UNITED STATES PATENT AND TRADEMARK OFFICE
CERTIFICATE OF CORRECTION

PATENT NO. : 5,220,026
DATED : June 15, 1993
INVENTOR(S) : YUKITERU MIMURA, ET AL.

It is certified that error appears in the above-identified patent and that said Letters Patent is hereby corrected as shown below:

COLUMN 20

Line 27, "(Compound 10)" should read --(Compound 10).--
        and close up left margin.

COLUMN 21

Line 5, "(Compound 11) should read --(Compound 11).--
        and close up left margin.

COLUMN 22

Line 5, "(Compound 12)" should read --(Compound 12).--.
    Line 41, "(Compound 13)" should read --(Compound 13).--
        and close up left margin.

COLUMN 23

Line 8, "(Compound 14)" should read --(Compound 14).--.

COLUMN 27

Line 20, "p" should read --p represents--.
    Line 21, "$-NR^{2a}R^{2b}$" should read -- $-NR^{2a}R^{2b}$,--.

COLUMN 28

Line 2, "$-(CH_2)_m-Y$" should read -- $-(CH_2)_m-Y$,--.
    Line 3, "m" should read --m represents--.
    Line 5, "wherein" should read --wherein each of--.
    Line 6, "alkyl" should read --alkyl,--.

UNITED STATES PATENT AND TRADEMARK OFFICE
CERTIFICATE OF CORRECTION

PATENT NO. : 5,220,026
DATED : June 15, 1993
INVENTOR(S) : YUKITERU MIMURA, ET AL.

It is certified that error appears in the above-identified patent and that said Letters Patent is hereby corrected as shown below:

COLUMN 28

Line 16, "and" should read --or-- and
"or" should read --and--.
Line 19, "and" should read --or-- and
"or" should read --and--.

Signed and Sealed this

Twelfth Day of April, 1994

Attest:

BRUCE LEHMAN

*Attesting Officer*

*Commissioner of Patents and Trademarks*

UNITED STATES PATENT AND TRADEMARK OFFICE
CERTIFICATE OF CORRECTION

PATENT NO. : 5,220,026
DATED : June 15, 1993
INVENTOR(S) : YUKITERU MIMURA ET AL.

It is certified that error appears in the above-indentified patent and that said Letters Patent is hereby corrected as shown below:

COLUMN 19

Line 66, "8-bromo-dimethylaminoethyl)amino" should read
--8-bromo-5-(2-dimethylaminoethyl)amino--.

Signed and Sealed this

Seventh Day of January, 1997

Attest:

BRUCE LEHMAN

Attesting Officer     Commissioner of Patents and Trademarks